United States Patent
Gimpelson

[19]

[11] Patent Number: 5,980,534
[45] Date of Patent: Nov. 9, 1999

[54] CERVICAL CLAMP

[76] Inventor: Richard J. Gimpelson, 1028 Terrace Rock Cir., Ballwin, Mo. 63011

[21] Appl. No.: 09/168,273

[22] Filed: Oct. 7, 1998

[51] Int. Cl.$^6$ .............................. A61B 17/42; A61B 17/46
[52] U.S. Cl. ............................................. 606/119; 606/120
[58] Field of Search .................................... 606/119, 120; 604/279

[56] References Cited

U.S. PATENT DOCUMENTS

| | | | |
|---|---|---|---|
| 2,400,251 | 5/1946 | Nagel | 128/361 |
| 3,358,677 | 12/1967 | Sheldon | 128/24 |
| 4,000,743 | 1/1977 | Weaver | 128/303 R |
| 5,037,430 | 8/1991 | Hasson | 606/119 |
| 5,059,198 | 10/1991 | Gimpelson | 606/119 |
| 5,108,408 | 4/1992 | Lally | 606/119 |
| 5,195,964 | 3/1993 | Kletzky et al. | 604/55 |
| 5,336,228 | 8/1994 | Cholhan | 606/119 |
| 5,520,704 | 5/1996 | Castro et al. | 606/208 |
| 5,562,680 | 10/1996 | Hasson | 606/119 |

OTHER PUBLICATIONS

Knutsson, F.: On the Technique of Urethrography. Acta Radiol., 10:437, 1929.

Brodny, M.L.: New Instrument for Urethography in Male. J. Urol., 46:350–354, 1941.

Gimpelson, R.J.: Preventing Cervical Reflux of the Distension Medium During Panoramic Hysteroscopy. The Journal of Reproductive Medicine, vol. 31 No. 7, Jul. 1996.

*Primary Examiner*—Gary Jackson
*Assistant Examiner*—Vy Q. Bui
*Attorney, Agent, or Firm*—Grace J. Fishel

[57] ABSTRACT

A cervical clamp for preventing reflux of a fluid medium such as carbon dioxide or a saline solution injected into a uterus. The clamp has a plurality of outwardly bowed, flexible fingers for gripping a cervix. The fingers operate between an open finger position for receiving the cervix and a closed finger position for grasping the cervix and radially compressing it against a sheath in the cervical canal through which the fluid medium is injected into the uterus.

8 Claims, 2 Drawing Sheets

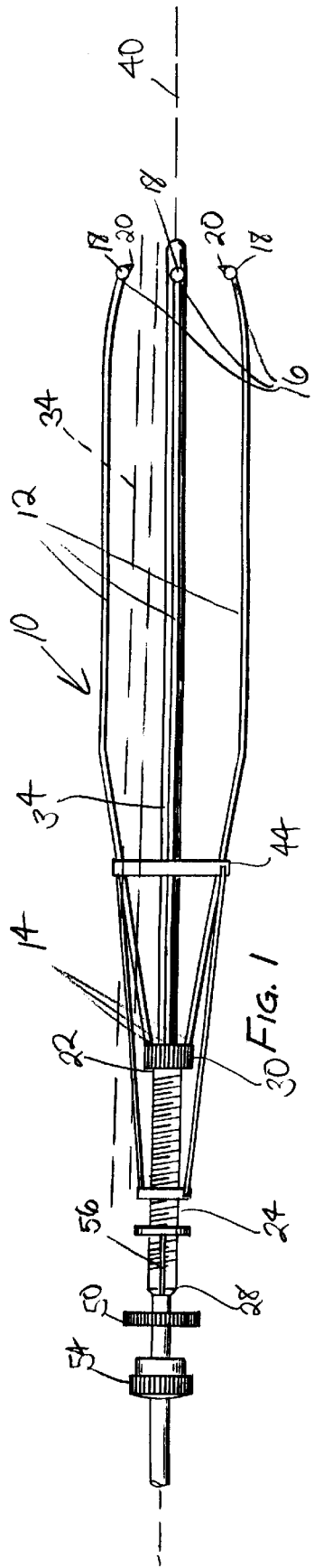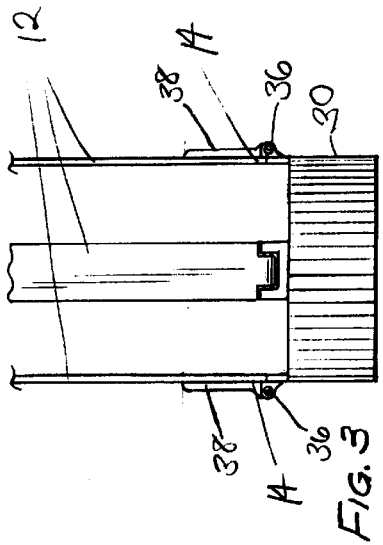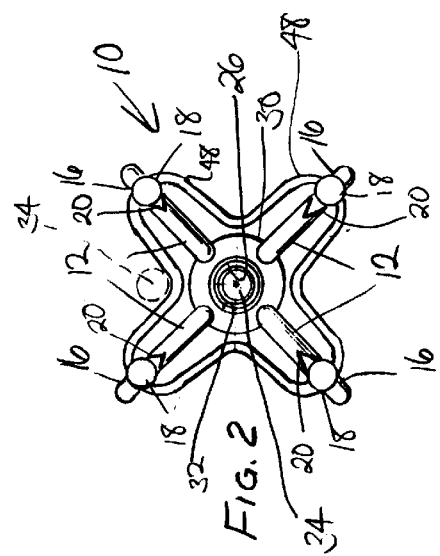

CERVICAL CLAMP

BACKGROUND OF THE INVENTION

1. Field of the Invention

The present invention relates to a cervical clamp for preventing reflux of a fluid medium injected into a uterus.

2. Brief Description of the Prior Art

There are various medical procedures which involve the injection of a fluid medium into the uterus. Included in this category are hysteroscopy and hysterosalpingography. In hysteroscopy, a thin sheath is inserted through the cervix into the uterine cavity. The sheath contains fiber optics that transmit light for viewing the uterine cavity and may also contain a biopsy, electrocautery or other instrument. With hysterosalpingography, x-rays are taken after a radiopaque dye has been injected through the cervix to outline the uterine cavity and fallopian tubes, often as part of an examination for causes of infertility.

Fluids are injected into the uterus in other procedures such as endometrial ablation and chromopertubation. In endometrial ablation, a solution is held in the uterus for visualization while the lining of the uterus is removed by treatment with laser or electrical energy or, possibly, by heating the solution injected into the uterus. Chromopertubation is similar to hysterosalpingography but done during a laparoscopic examination wherein the cervix is sealed and a dye is injected to verify the patency of the fallopian tubes.

The practice of the above procedures involves sealing the walls of a cervical canal around a sheath delivering the fluid medium such that the medium does not reflux around the sheath's exterior back through the cervix. Numerous devices have been developed to prevent reflux, but they are either difficult to use or limit the shape and diameter of the sheath passing through the cervix, or they restrict the movement of instruments in the uterus once the sheath has been inserted into the cervical canal and/or interfere with palpitory information available to the operating physician.

For example, a tenaculum with two pivotally mounted arms with inwardly directed spikes has been used in hysteroscopic examination. The gripping action is performed solely by the spikes digging into the cervix and pressing it against the sheath, causing bleeding, trauma and pain for the patient. It is sometimes necessary to use two of these tenacula, filling the vagina and further limiting the movement of the sheath and other instruments which may pass through it.

Other devices sealably engage a cone (called an "acorn") with the outside opening of the cervical canal by means of a sliding vacuum cup connected to a vacuum port. Once the vacuum cup is evacuated, it seals with the cervix, pushing the acorn into the outside opening. One major problem with this type of device is that there is frequently a mismatch between the size of the cup and the size of the cervix. The device also limits movement of the sheath in the vaginal canal and requires a source of vacuum which may be noisy, such as a vacuum pump, or leak, such as a vacuum syringe.

An inflatable balloon for inflation in the cervical canal or a pair of balloons for inflation, one on the outside opening of the canal and one on the inside have been provided on the sheath inserted through the cervical canal. Once the sheath has been inserted and the balloon(s) inflated, the sheath cannot be further moved. In addition, the sheath carrying the balloon(s) must be relatively large so it is difficult for the operating physician to insert it through the cervical canal.

The best device heretofore known to the applicant is a tenaculum described in *The Journal of Reproductive Medicine*, Vol. 31, No. 7, July 1986 and in U.S. Pat. No. 5,059,198. The tenaculum described therein purses the cervix against the sheath by squeezing it into an oval at opposite side edges. A better seal might be obtained if the cervix were compressed radially against the sheath, the previous tenaculum, not providing this action.

BRIEF SUMMARY OF THE INVENTION

In view of the above, it is an object of the present invention to provide an easy-to-use cervical clamp for effectively sealing the walls of a cervical canal around a sheath delivering fluid medium into a uterus. It is another object to provide a cervical clamp that allows the sheath to be moved in the cervical canal or uterus without breaking the seal and without interfering with palpitory information available to the operating physician. Other objects and features of the invention will be in part apparent and in part pointed out hereinafter.

In accordance with the invention, a cervical clamp for preventing reflux of a fluid medium injected into a uterus has an elongated externally threaded member with a proximate and a distal end. A plurality of outwardly bowed, flexible fingers, each finger having a generally inwardly bent, pointed distal end and being radially connected at a proximate end to the distal end of the elongated threaded member. The fingers extend from a cervix to outside a vagina.

A nut is threaded on the externally threaded member and a hollow tubular member. The hollow tubular member slides over the fingers between an open finger position for receiving the cervix and a closed finger position for grasping the cervix and radially compressing it against a sheath in a cervical canal through which a fluid medium can be injected to a uterus. The clamp prevents reflux of the fluid medium between the sheath and the cervical canal.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which:

FIG. 1 is a side elevation of a clamp in accordance with the present invention, illustrated with a sheath passing through the center of the clamp;

FIG. 2 is a right end view of the clamp as shown in FIG. 1;

FIG. 3 is a detail on an enlarged scale taken along line 3—3 in FIG. 5;

DETAILED DESCRIPTION OF THE INVENTION

Figures 4, 5:
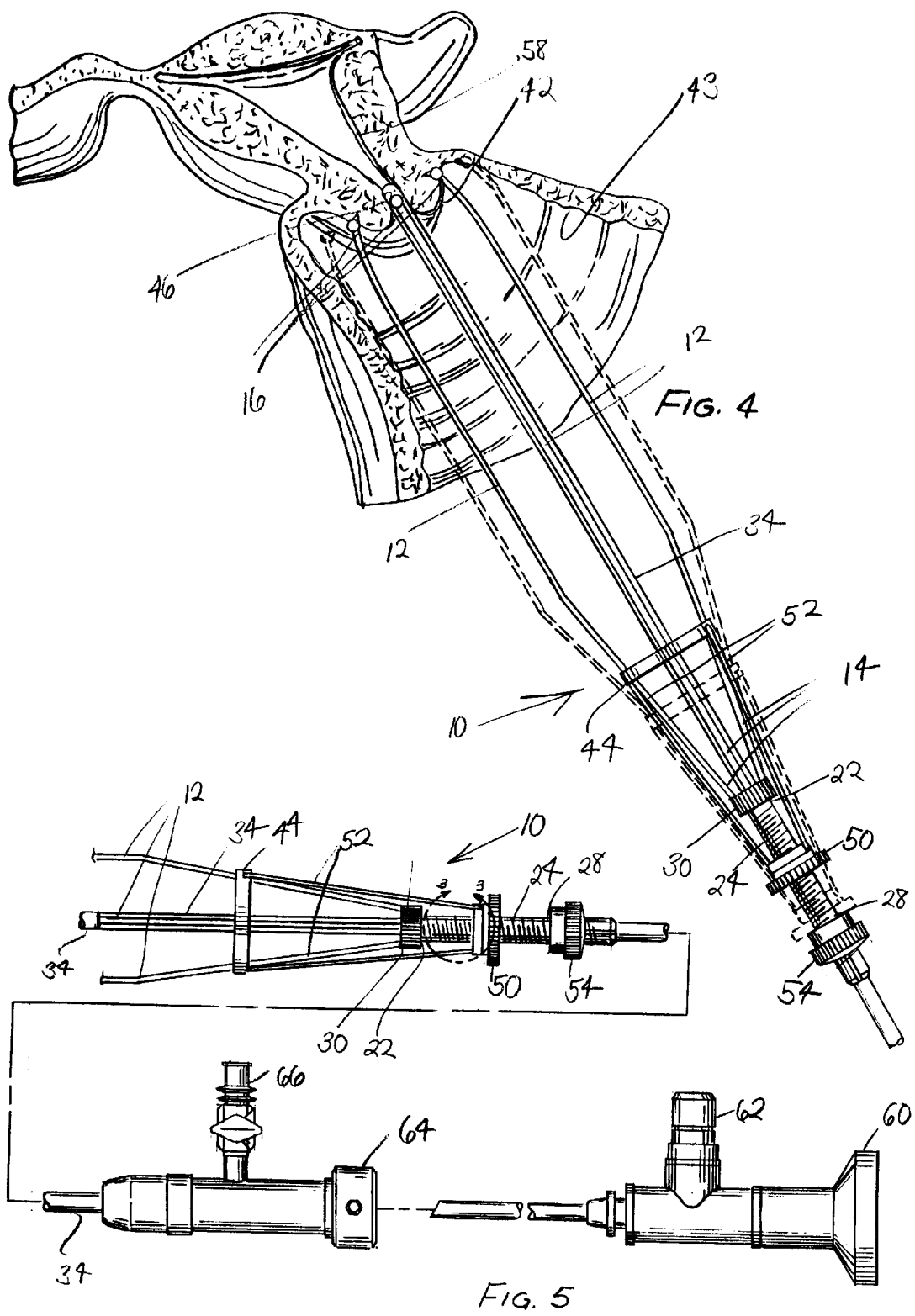
FIG. 4 is a perspective view of the clamp being clamped on a cervix for sealing a cervical canal to the sheath and for preventing reflux of fluid medium around the sheath; and, FIG. 5 is an exploded side elevation of the clamp with a with a hysteroscope.
Figures 4, 5:
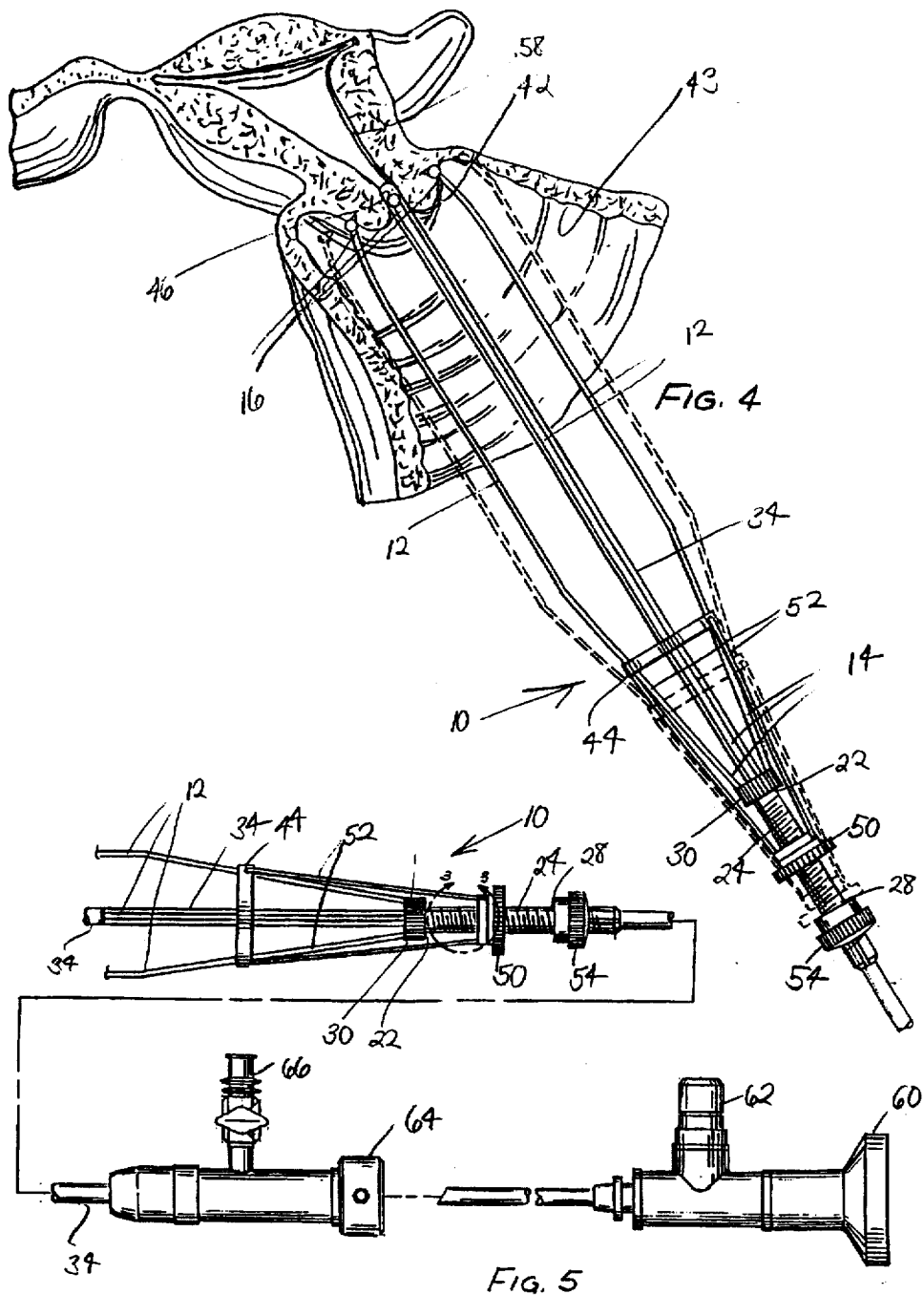

Referring to the drawings more particularly by reference character, reference numeral 10 refers to a cervical clamp in accordance with the present invention. Clamp 10 has a plurality of outwardly bowed, flexible fingers 12. Fingers 12 may be formed of spring steel or the like and have proximal and distal ends 14, 16, respectively. At distal end 16, fingers 12 are pointed and generally inwardly bent. As best seen in FIG. 2, the pointed distal end of fingers 12 has a knob 18 with an integral tooth 20 of generally conical shape projecting therefrom. As will be apparent, knob 18 backs tooth 20 and prevents the penetration of the tooth into the flesh of the cervix for any distance greater than the length of the tooth. Knob 18 also spreads the load over the cervical tissue gripped by clamp 10, reducing the amount of tearing.

Proximal end 14 of fingers 12 is connected to a distal end 22 of an elongated externally threaded member 24. As illustrated in the drawings, externally threaded member 24 has a longitudinal passageway 26 (see FIG. 2) running between distal end 22 and a proximal end 28 of the member, in which form externally threaded member 24 comprises a hollow threaded sleeve with a cap 30 which is welded, threaded or otherwise attached to the distal end of the member. Cap 30 has an aperture 32 (see FIG. 2) axially aligned with passageway 26 through which a sheath 34 may be passed for use as more particularly described below, whereafter it will also become apparent that member 22 may be formed, in other embodiments, without passageway 26.

Fingers 12 are preferably circumferentially and equally spaced relative to one another about distal end 22 of externally threaded member 24. There are at least three and preferably four fingers 12, in which instance fingers 12 are spaced relative to one another by approximately 90 degrees. Fingers 12 may be set in holes provided for that purpose in cap 30, welded or otherwise attached to externally threaded member 24. In some cases, it may be preferred that fingers 12 be hinged as shown in FIG. 3. As illustrated in this view, a hinge 36 has a stop 38 limiting folding of fingers 12 inwardly beyond parallel to a longitudinal axis 40 (see FIG. 1) of the externally threaded member 24. As will become apparent, hinge 36 may be provided to assist dislodging of clamp 10 from a cervix 42 upon completion of a procedure. Fingers 12 reach from cervix 42 to outside a vagina 43 where clamp 10 can be manipulated by the operator.

A hollow tubular member 44 is positioned around fingers 12 for sliding over the fingers and moving them between an open finger position as shown in broken lines in FIG. 4 for receiving cervix 42 and a closed finger position as shown in full lines for grasping the cervix and radially compressing it against sheath 34 inserted in a cervical canal 46. Hollow tubular member 44 may be a ring with lobes 48 as shown in FIG. 2, in which form sheath 34 may be received between lobes 48, generally parallel to but outside of hollow tubular member 44 (see FIGS. 1–2).

Hollow tubular member 44 is connected to a nut 50 by a pair of struts 52, while nut is threaded on externally threaded member 22 for opening and closing fingers 12. This arrangement is preferred for purposes of facilitating easy cleaning of clamp 10 but it will be understood that the same function can be achieved when hollow tubular member 44 and nut 50 are integrally formed. In which case, hollow tubular member 44 is elongated and internally threaded. The claims which follow will therefore be understood to include this possibility.

When externally threaded member 24 is a hollow threaded sleeve, the threads may taper towards proximal end 28 for receipt of a locking nut 54. In which case, distal end 22 has at least one slit 56 for tightening the externally threaded member on sheath 34 in passageway 26 as locking nut 54 is tightened on the distal end. Preferably a plurality, such as three, circumferentially, equally spaced slits 56 are provided for this purpose.

As immediately apparent from FIGS. 2 and 4, clamp 10 radially compresses cervix 42 against sheath 34 in cervical canal 46 as fingers 12 are compressed by hollow tubular member 44. For which purpose, as above described, clamp 10 must have at least three fingers 12, preferably four and possibly more fingers. By circumferentially applying pressure on the cervix at spaced intervals, the cervical canal is effectively sealed against sheath 34 blocking reflux of a fluid injected through sheath 34 into a uterus 58. Whether sheath 34 passes through passageway 26 or between lobes 48 on the outside of hollow tubular member 44, the sheath may be moved in the vaginal canal by the operating physician without losing the seal and without loss of palpitory information as the sheath passes through the canal and into the uterus. As will be appreciated by operating physicians, palpitory information provides useful feedback helping the operator to avoid injuring the walls of the canal or uterus or puncturing them. The combination of features provided by clamp 10 is not found in any of the prior art devices.

In FIG. 5, clamp 10 is illustrated for use in hysteroscopy. A telescope 60 with an attached light post 62 is inserted in sheath 34 and attached with a locking ring 64. Sheath 34 includes an insufflation channel 66. The hysteroscope shown in FIG. 5 is for diagnostic use, for operating purposes sheath 34 additionally has an operating port (not shown). There a number of different types of sheaths 34, differing in size, shape, number of internal channels, etc., variations known to those performing hysteroscopy. When the procedure is a hysteroscopy, the fluid medium injected into the uterus is a distension medium such as carbon dioxide, saline solution, dextran solution (e.g., Dextran 70 or HYSKON™ liquid solution), sorbitol solution, mannitol solution, glycine solution, lactate solution (e.g., Ringer's lactate solution), etc.

While clamp 10 is illustrated for use with a hysteroscope in FIG. 5, it will be understood that it can be used in other procedures which involve the injection of a fluid medium into a uterus such as hysterosalpingography, endometrial ablation, chromopertubation, etc. Clamp 10 can be used for pressing an acorn tip into the outside of the vaginal canal, in addition or as an alternative to pressing the cervix against the sheath. Other utilities include use of clamp 10 as a uterine manipulator. When sheath 34 is locked in passageway 26, the sheath can be used for positioning the uterus, making the right or left fallopian tube more accessible for tubal ligation. Other such utilities are also possible, clamp 10, however, being primarily designed for preventing reflux of a fluid medium injected into the uterus.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

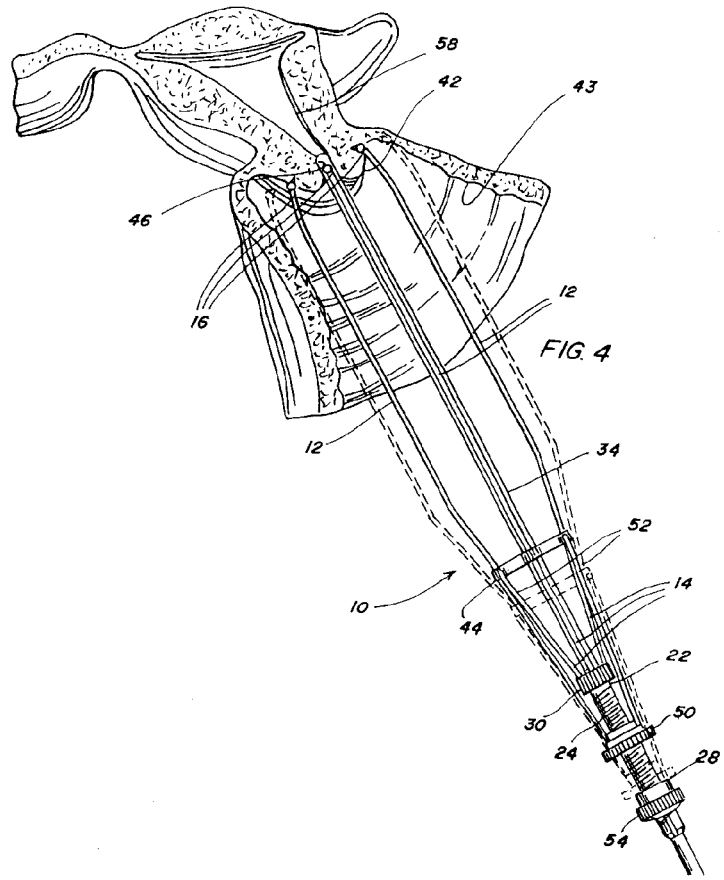

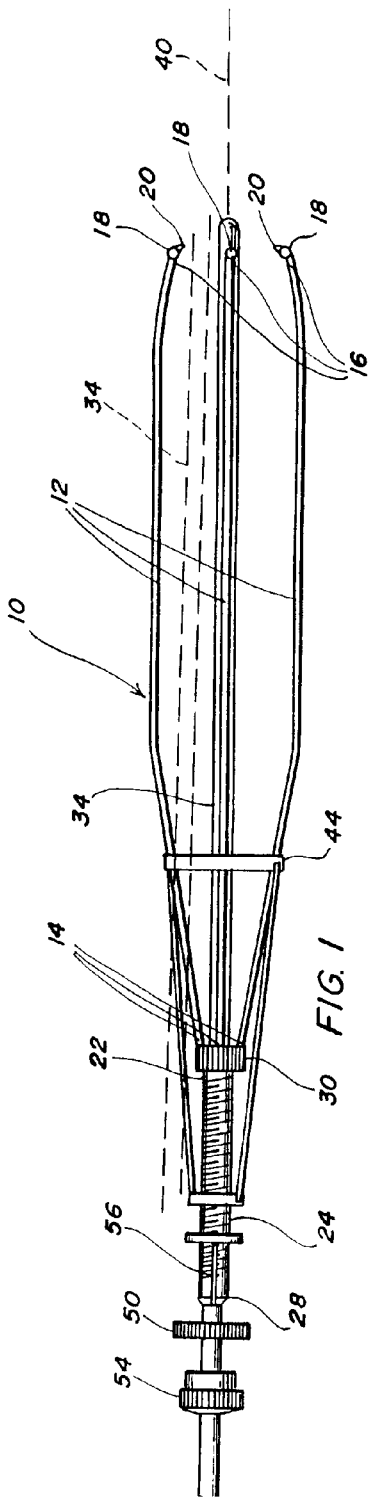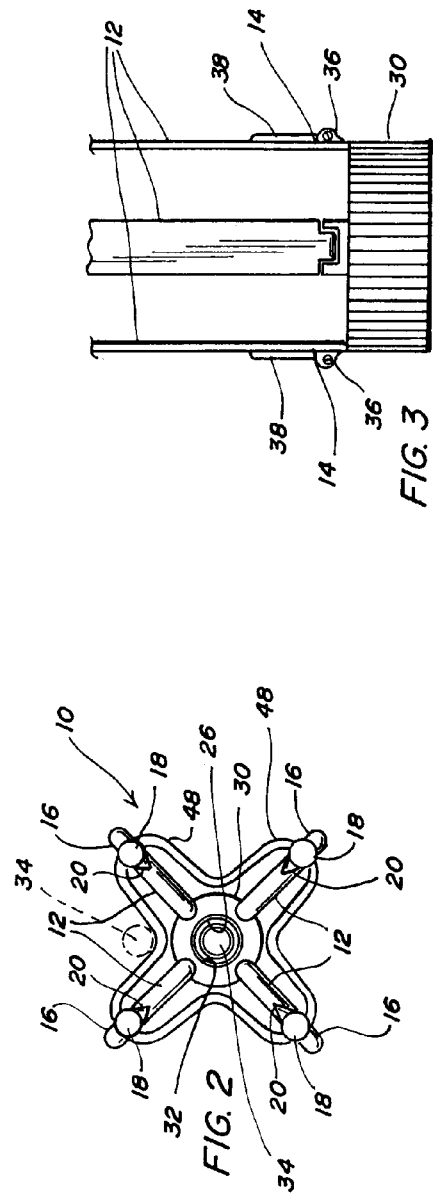

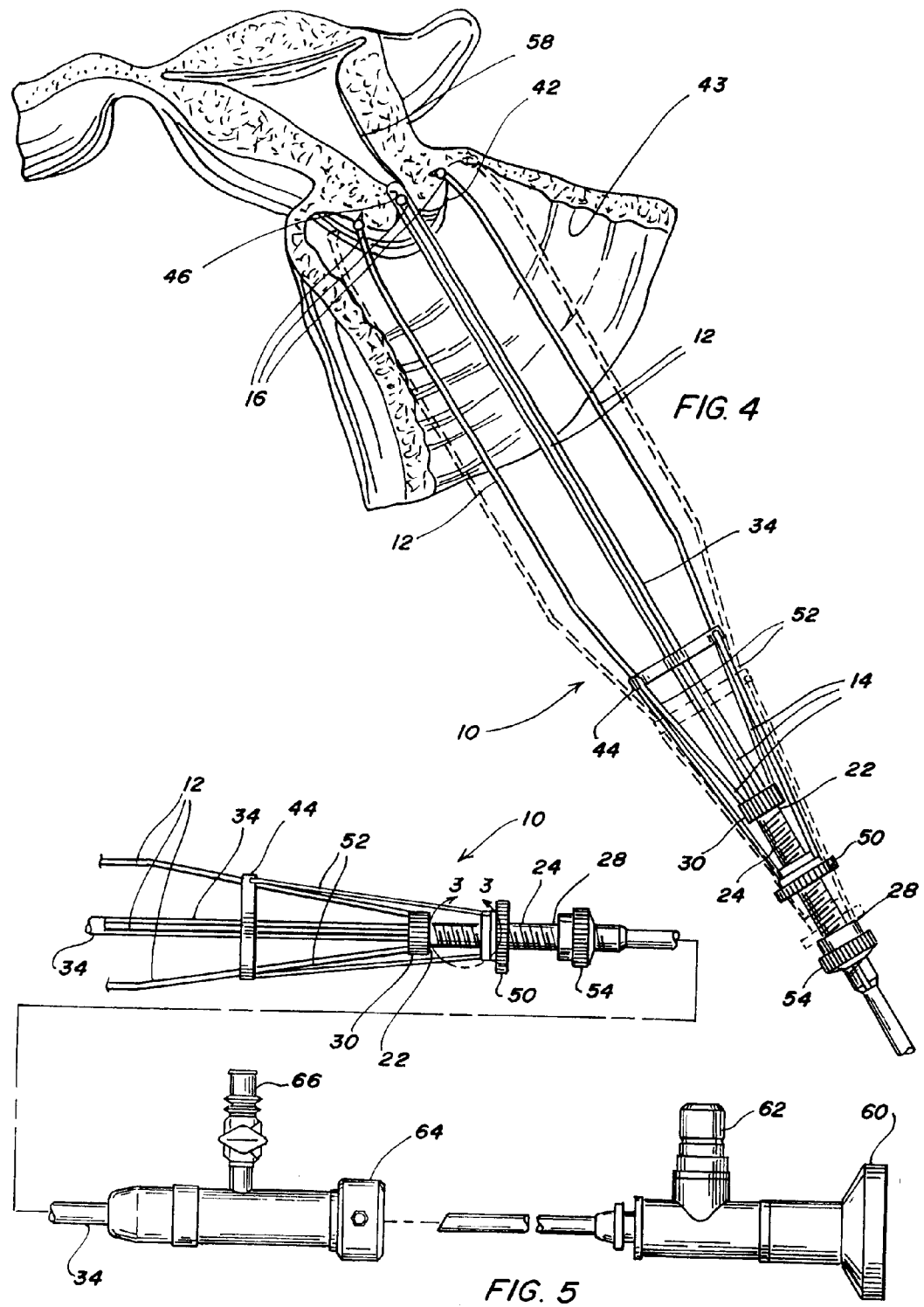

What is claimed:

1. A cervical clamp for preventing reflux of a fluid medium injected into a uterus, said clamp comprising an elongated externally threaded member with a proximal and a distal end;

a plurality of outwardly bowed, flexible fingers, each finger having a generally inwardly bent, pointed distal end and being radially connected at a proximal end to the distal end of the elongated threaded member, said fingers adapted to extend from a cervix through a vagina;

a nut threaded on the externally threaded member; and, a hollow tubular member connected to the nut for sliding over the fingers between an open finger position for receiving a cervix and a closed finger position for grasping a cervix and radially compressing a cervix against a sheath in a cervical canal through which a fluid medium is injected into a uterus, said clamp preventing reflux of the fluid medium between the sheath and the cervical canal.

2. The cervical clamp of claim 1 wherein the pointed distal end of each finger comprises a knob with an integral tooth.

3. The cervical clamp of claim 1 wherein the externally threaded member has an open, longitudinal passageway running between said proximal and distal ends, said passageway for accommodating a sheath for insertion into a cervical canal, said sheath movable in the passageway.

4. The cervical clamp of claim 3 wherein the externally threaded member has a tapered diameter and at least one longitudinal slit at the proximal end, said clamp further comprising a locking nut threaded on the proximal end for tightening the externally threaded member on a sheath in the passageway.

5. The cervical clamp of claim 1 wherein the hollow tubular member has one or more lobes between which a sheath can be inserted.

6. The cervical clamp of claim 1 wherein a hinge connects the proximal end of each finger to the distal end of the elongated threaded member, said hinge having a stop limiting folding of the finger inwardly beyond generally parallel to a longitudinal axis of the elongated threaded member.

7. A cervical clamp for preventing reflux of a fluid medium injected into a uterus, said clamp comprising an elongated externally threaded member with a proximal and a distal end and an open, longitudinal passageway running between said proximal and distal ends, said passageway for accommodating a sheath for insertion into a cervical canal, said sheath movable in the passageway;

a plurality of outwardly bowed, flexible fingers, each finger having a generally inwardly bent, pointed distal end with a knob and an integral tooth and being radially connected at a proximal end to the distal end of the elongated threaded member, said fingers adapted to extend from a cervix through a vagina;

a nut threaded on the externally threaded member; and, a hollow tubular member connected to the nut by two or more struts for sliding over the fingers between an open finger position for receiving a cervix and a closed finger position for grasping a cervix and radially compressing a cervix against a sheath in a cervical canal through which a fluid medium is injected into a uterus, said clamp preventing reflux of the fluid medium between the sheath and the cervical canal.

8. The cervical clamp of claim 7 wherein the externally threaded member has a tapered diameter and at least one longitudinal slit at the proximal end, said clamp further comprising a locking nut threaded on the proximal end for tightening the externally threaded member on a sheath in the passageway.

\* \* \* \* \*

UNITED STATES PATENT AND TRADEMARK OFFICE
CERTIFICATE OF CORRECTION

Page 1 of 4

PATENT NO. : 5,980,534
DATED : November 9, 1999
INVENTOR(S) : Richard J. Gimpelson It is certified that error appears in the above-identified patent and that said Letters Patent is hereby corrected as shown below:

The title page, should be deleted to be replaced with the attached title page:

The drawing sheets, consisting of Figs.1-5, should be deleted to be replaced with the drawing sheets, consisting of Figs. 1-5, as shown on the attached pages.

Signed and Sealed this

Thirtieth Day of May, 2000

*Attest:*

Q. TODD DICKINSON

*Attesting Officer*          *Director of Patents and Trademarks*

United States Patent [19]
Gimpelson

[11] Patent Number: 5,980,534
[45] Date of Patent: Nov. 9, 1999

[54] CERVICAL CLAMP

[76] Inventor: Richard J. Gimpelson, 1028 Terrace Rock Cir., Ballwin, Mo. 63011

[21] Appl. No.: 09/168,273

[22] Filed: Oct. 7, 1998

[51] Int. Cl.⁶ ............................ A61B 17/42; A61B 17/46
[52] U.S. Cl. ........................................... 606/119; 606/120
[58] Field of Search .................................. 606/119, 120; 604/279

[56] References Cited

U.S. PATENT DOCUMENTS

| | | | |
|---|---|---|---|
| 2,400,251 | 5/1946 | Nagel | 128/361 |
| 3,358,677 | 12/1967 | Sheldon | 128/24 |
| 4,000,743 | 1/1977 | Weaver | 128/303 R |
| 5,037,430 | 8/1991 | Hasson | 606/119 |
| 5,059,198 | 10/1991 | Gimpelson | 606/119 |
| 5,108,408 | 4/1992 | Lally | 606/119 |
| 5,195,964 | 3/1993 | Kletzky et al. | 604/55 |
| 5,336,228 | 8/1994 | Cholhan | 606/119 |
| 5,520,704 | 5/1996 | Castro et al. | 606/208 |
| 5,562,680 | 10/1996 | Hasson | 606/119 |

OTHER PUBLICATIONS

Knutsson, F.: On the Technique of Urethrography. Acta Radiol., 10:437, 1929.

Brodny, M.L.: New Instrument for Urethography in Male. J. Urol., 46:350–354, 1941.

Gimpelson, R.J.: Preventing Cervical Reflux of the Distension Medium During Panoramic Hysteroscopy. The Journal of Reproductive Medicine, vol. 31 No. 7, Jul. 1996.

*Primary Examiner*—Gary Jackson
*Assistant Examiner*—Vy Q. Bui
*Attorney, Agent, or Firm*—Grace J. Fishel

[57] ABSTRACT

A cervical clamp for preventing reflux of a fluid medium such as carbon dioxide or a saline solution injected into a uterus. The clamp has a plurality of outwardly bowed, flexible fingers for gripping a cervix. The fingers operate between an open finger position for receiving the cervix and a closed finger position for grasping the cervix and radially compressing it against a sheath in the cervical canal through which the fluid medium is injected into the uterus.

8 Claims, 2 Drawing Sheets

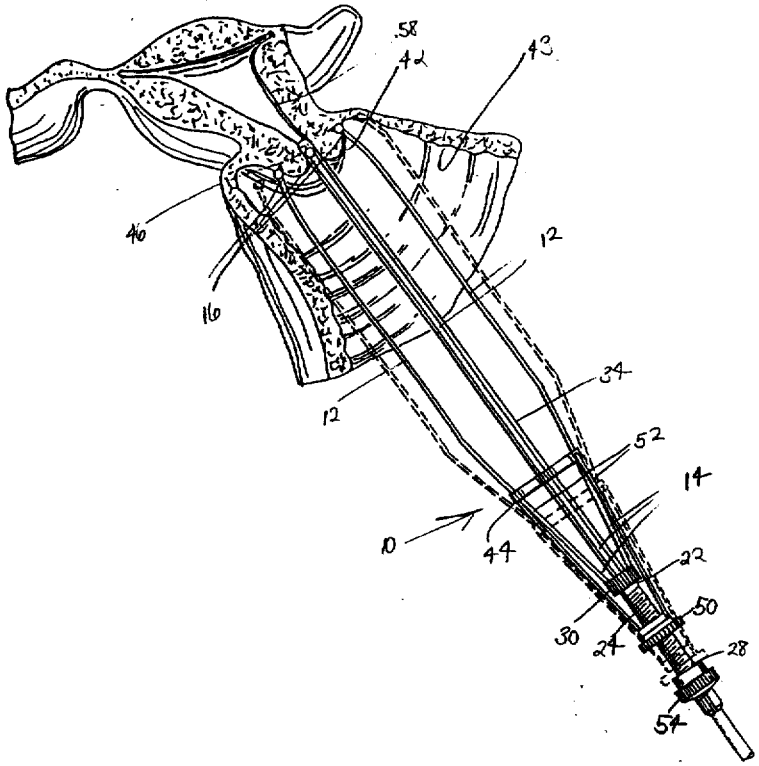

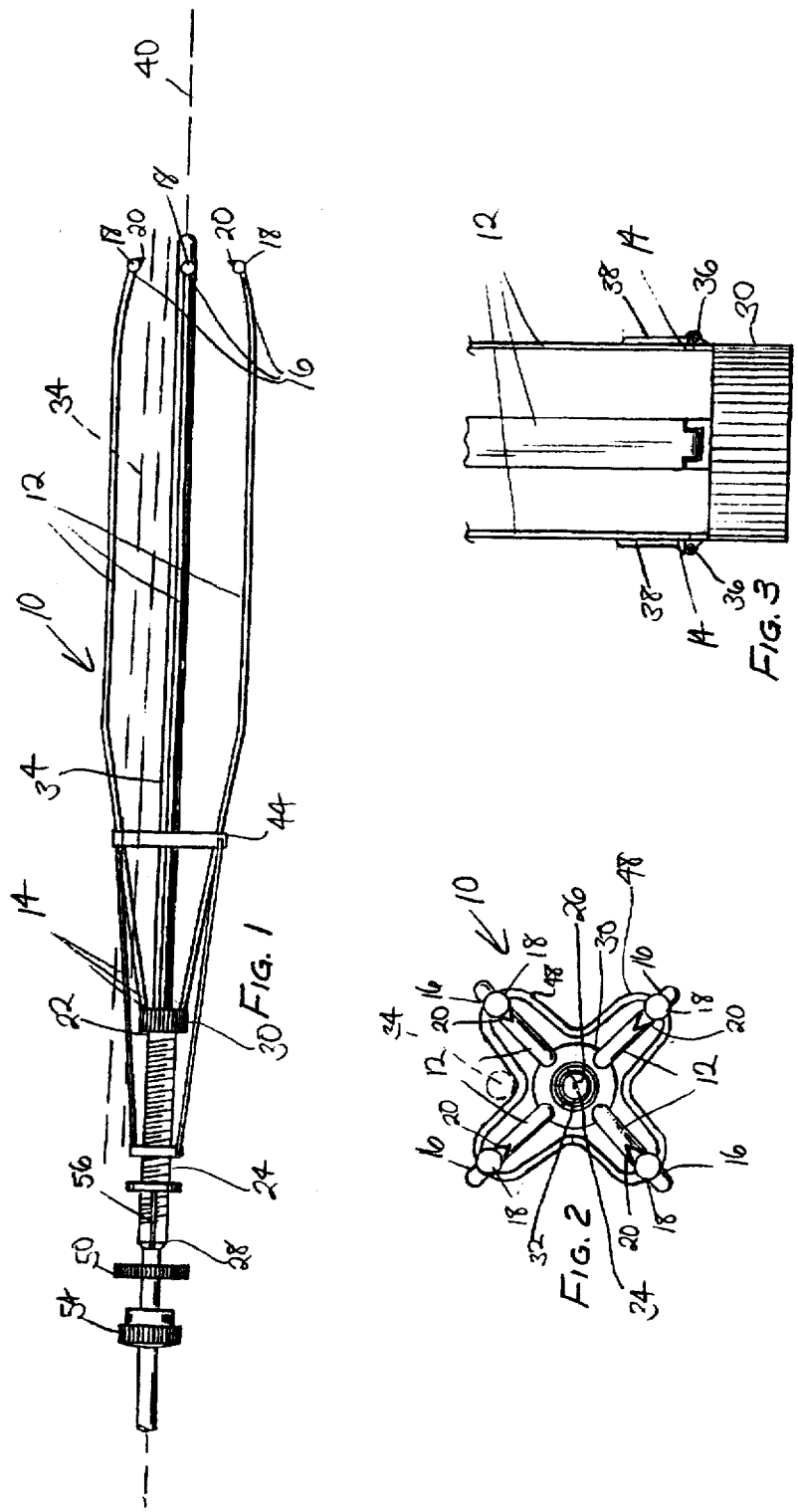

UNITED STATES PATENT AND TRADEMARK OFFICE
CERTIFICATE OF CORRECTION

PATENT NO.   : 5,980,534
DATED        : November 9, 1999
INVENTOR(S)  : Richard J. Gimpelson It is certified that error appears in the above-identified patent and that said Letters Patent is hereby corrected as shown below:

Delete the title page and insert therefore the attached title page.

Delete Drawing Sheets 1 and 2 and insert therefore the attached Drawing Sheets 1 and 2.

This certificate supersedes Certificate of Correction issued May 30, 2000.

Signed and Sealed this

Fifth Day of August, 2003

JAMES E. ROGAN
*Director of the United States Patent and Trademark Office*

United States Patent [19]
Gimpelson

[11] Patent Number: 5,980,534
[45] Date of Patent: Nov. 9, 1999

[54] CERVICAL CLAMP

[76] Inventor: Richard J. Gimpelson, 1028 Terrace Rock Cir., Ballwin, Mo. 63011

[21] Appl. No.: 09/168,273
[22] Filed: Oct. 7, 1998
[51] Int. Cl.[6] .......................... A61B 17/42; A61B 17/46
[52] U.S. Cl. .......................................... 606/119; 606/120
[58] Field of Search .................................. 606/119, 120; 604/279

[56] References Cited

U.S. PATENT DOCUMENTS

| | | | |
|---|---|---|---|
| 2,400,251 | 5/1946 | Nagel | 128/361 |
| 3,358,677 | 12/1967 | Sheldon | 128/24 |
| 4,000,743 | 1/1977 | Weaver | 128/303 R |
| 5,037,430 | 8/1991 | Hasson | 606/119 |
| 5,059,198 | 10/1991 | Gimpelson | 606/119 |
| 5,108,408 | 4/1992 | Lally | 606/119 |
| 5,195,964 | 3/1993 | Kletzky et al. | 604/55 |
| 5,336,228 | 8/1994 | Cholhan | 606/119 |
| 5,520,704 | 5/1996 | Castro et al. | 606/208 |
| 5,562,680 | 10/1996 | Hasson | 606/119 |

OTHER PUBLICATIONS

Knutsson, F.: On the Technique of Urethrography. Acta Radiol., 10:437, 1929.

Brodny, M.L.: New Instrument for Urethography in Male. J. Urol., 46:350–354, 1941.

Gimpelson, R.J.: Preventing Cervical Reflux of the Distension Medium During Panoramic Hysteroscopy. The Journal of Reproductive Medicine, vol. 31 No. 7, Jul. 1996.

*Primary Examiner*—Gary Jackson
*Assistant Examiner*—Vy Q. Bui
*Attorney, Agent, or Firm*—Grace J. Fishel

[57] ABSTRACT

A cervical clamp for preventing reflux of a fluid medium such as carbon dioxide or a saline solution injected into a uterus. The clamp has a plurality of outwardly bowed, flexible fingers for gripping a cervix. The fingers operate between an open finger position for receiving the cervix and a closed finger position for grasping the cervix and radially compressing it against a sheath in the cervical canal through which the fluid medium is injected into the uterus.

8 Claims, 2 Drawing Sheets